US010111867B2

(12) United States Patent
Marom et al.

(10) Patent No.: US 10,111,867 B2
(45) Date of Patent: Oct. 30, 2018

(54) PROCESS AND INTERMEDIATES FOR THE PREPARATION OF PERAMPANEL

(71) Applicant: MAPI PHARMA LTD., Ness Ziona (IL)

(72) Inventors: Ehud Marom, Tel Aviv (IL); Shai Rubnov, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 15/543,363

(22) PCT Filed: Feb. 17, 2015

(86) PCT No.: PCT/IL2015/050180
§ 371 (c)(1),
(2) Date: Jul. 13, 2017

(87) PCT Pub. No.: WO2016/132343
PCT Pub. Date: Aug. 25, 2016

(65) Prior Publication Data
US 2018/0008584 A1 Jan. 11, 2018

(51) Int. Cl.
*A61K 31/444* (2006.01)
*C07D 213/64* (2006.01)
*C07D 401/04* (2006.01)

(52) U.S. Cl.
CPC .......... *A61K 31/444* (2013.01); *C07D 213/64* (2013.01); *C07D 401/04* (2013.01)

(58) Field of Classification Search
CPC .................................................. C07D 213/02
See application file for complete search history.

(56) References Cited

U.S. PATENT DOCUMENTS

| 6,949,571 | B2 | 9/2005 | Nagato |
| 7,524,967 | B2 | 4/2009 | Koyakumaru |
| 7,563,811 | B2 | 7/2009 | Nagato |
| 7,718,807 | B2 | 5/2010 | Nagato |
| 7,803,818 | B2 | 9/2010 | Omae |
| 7,939,549 | B2 | 5/2011 | Nagato |
| 8,772,497 | B2 | 7/2014 | Arimoto |
| 2008/0312284 | A1 | 12/2008 | Omae |
| 2009/0088574 | A1 | 4/2009 | Urawa |
| 2010/0324297 | A1 | 12/2010 | Arimoto |

FOREIGN PATENT DOCUMENTS

| CN | 103980188 A | 8/2014 | |
| EP | 1300396 A1 | 4/2003 | |
| EP | 1764361 A1 | 3/2007 | |
| IL | 152848 | 9/2007 | |
| WO | 03047577 A2 | 6/2003 | |
| WO | WO 2003/047577 | * 6/2003 | ............. A61K 31/44 |
| WO | 2007072868 A1 | 6/2007 | |
| WO | 2012102580 A1 | 8/2012 | |
| WO | 2013102897 A1 | 7/2013 | |
| WO | 2015013520 A1 | 1/2015 | |

OTHER PUBLICATIONS

Augustine et al., (2009) "Propylphosphonic anhydride (T3P®): A remarkably efficient reagent for the one-pot transformation of aromatic, heteroaromatic, and aliphatic aldehydes to nitriles". Synlett, 2009(20), pp. 3378-3382.
Brittain HG (1999) "Polymorphism in Pharmaceutical Solids", Marcel Dekker, Inc., chapter 5, parts B and C, pp. 188-195.
Chandrasekhar & Gopalaiah, (2003) Beckmann reaction of oximes catalysed by chloral: mild and neutral procedures. Tetrahedron letters, 44(4), pp. 755-756.
De Luca et al., (2002) Beckmann rearrangement of oximes under very mild conditions. The Journal of organic chemistry, 67(17), pp. 6272-6274.
El-Faham et al., (2013) An efficient and mild method for the synthesis and hydrazinolysis of N-glyoxylamino acid esters. Journal of Chemistry, vol. 2013 (article ID 901745) pp. 1-7.
Grossman & Gelman, (2006) Novel trans-spanned palladium complexes as efficient catalysts in mild and amine-free cyanation of aryl bromides under air. Organic letters, 8(6), pp. 1189-1191.
Kim et al., (2012) Synthesis of Aromatic Nitriles Using Nonmetallic Cyano-Group Sources. Angewandte Chemie International Edition, 51, pp. 11948-11959.
Sharghi & Sarvari, (2003) Graphite as an efficient catalyst for one-step conversion of aldehydes into nitriles in dry media. Synthesis, 2003(02), pp. 243-246.
Veisi, (2010) Direct oxidative conversion of alcohols, amines, aldehydes, and benzyl halides into the corresponding nitriles with trichloroisocyanuric acid in aqueous ammonia. Synthesis, 2010(15), pp. 2631-2635.
Weissman et al., (2005) Ligand-free palladium-catalyzed cyanation of aryl halides. The Journal of organic chemistry, 70, pp. 1508-1510.
Yeung et al., (2010) A Mild and Efficient Palladium-Catalyzed Cyanation of Aryl Mesylates in Water or tBuOH/Water. Angewandte Chemie, 122, pp. 9102-9106.
Zanon et al., (2003) Copper-catalyzed domino halide exchange-cyanation of aryl bromides. Journal of the American Chemical Society, 125, pp. 2890-2891.
Zhang et al., (1996) An improved preparation method of benzyl and thenyl triphenylphosphonium salts. Synthetic communications, 26(16), pp. 3091-3095.

(Continued)

*Primary Examiner* — Erich A Leeser

(74) *Attorney, Agent, or Firm* — Rothwell, Figg, Ernst & Manbeck, P.C.

(57) ABSTRACT

The present invention describes a process for the synthesis of 3-(2-cyanophenyl)-5-(2-pyridyl)-1-phenyl-1,2-di-hydropyridin-2-one (Perampanel) represented by the structure of formula (1), and salts thereof, especially salts with pharmaceutically acceptable acids. The present invention further relates to certain intermediates formed and/or used in such process.

21 Claims, No Drawings

(56) References Cited

OTHER PUBLICATIONS

Zhou et al., (2009) A general and convenient catalytic synthesis of nitriles from amides and silanes. Organic letters, 11(11), pp. 2461-2464.
Zhu et al., (2007) An efficient new procedure for the one-pot conversion of aldehydes into the corresponding nitriles. Synlett, 2007(08), pp. 1317-1319.
Cartier et al., (2003) New, Regioselective, One-Pot Synthesis of (all-E)-Retinoic Acid and Analogues from Enaminodiester Synthons. European Journal of Organic Chemistry 2003(12): 2250-2253.
Lee et al., (2015) Virtually instantaneous, room-temperature [(11)C]-cyanation using biaryl phosphine Pd(0) complexes. J Am Chem Soc 137(2): 648-651.
Lee et al., (2015) Virtually instantaneous, room-temperature [(11)C]-cyanation using biaryl phosphine Pd(0) complexes. J Am Chem Soc 137(2): 648-651. Supporting Information, table of contents general procedures for reactions in table 1; pp. S1-S98. Retrieved from the Internet: URL: https://www.pubs.acs.org/doi/suppl/10.1021/ja512115s/suppl_file/ja512115s_si_001.pdf, on Jun. 11, 2018.
Extended European Search Report issued in EP 15882498.7 dated Jun. 28, 2018, 9 pages.

\* cited by examiner

PROCESS AND INTERMEDIATES FOR THE PREPARATION OF PERAMPANEL

CROSS-REFERENCE TO RELATED APPLICATIONS

The present application is a national stage filing under 35 U.S.C. § 371 of PCT/IL2015/050180, filed on Feb. 17, 2015. Each application is incorporated herein by reference in its entirety.

FIELD OF THE INVENTION

The present invention relates to a process for the preparation of Perampanel and its salts with physiologically acceptable acids. The present invention further relates to certain intermediates formed in such process.

BACKGROUND OF THE INVENTION

Perampanel (Fycompa; E 2007) is a highly selective, non-competitive AMPA (alpha-amino-3-hydroxy-5-methyl-4-isoxazolepropionic acid)-type glutamate receptor antagonist used for adjunctive treatment of partial-onset seizures, with or without secondarily generalized seizures, in patients with epilepsy aged 12 years and older. Perampanel is chemically designated 5'-(2-cyanophenyl)-1'-phenyl-2,3'-bipyridinyl-6'(1'H)-one or 3-(2-cyanophenyl)-5-(2-pyridyl)-1-phenyl-1,2-dihydropyridin-2-one, and is represented by the following chemical structure:

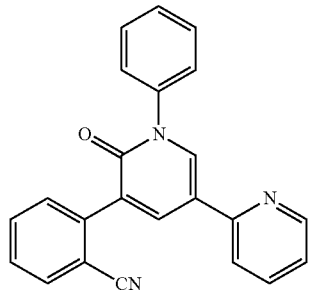 [SMILES: N#Cc1ccccc1-c1cc(-c2ccccn2)cn(-c2ccccc2)c1=O]

EP1300396, WO 03/047577, US 2010/0324297, WO 2007/072868 and U.S. Pat. No. 7,524,967 disclose processes for preparing of Perampanel by sequential combination of fragments (A), (B) and (C) with a 1,2-dihydro-pyridin-2-one core, using palladium-catalyzed reactions (generally represented in Scheme 1):

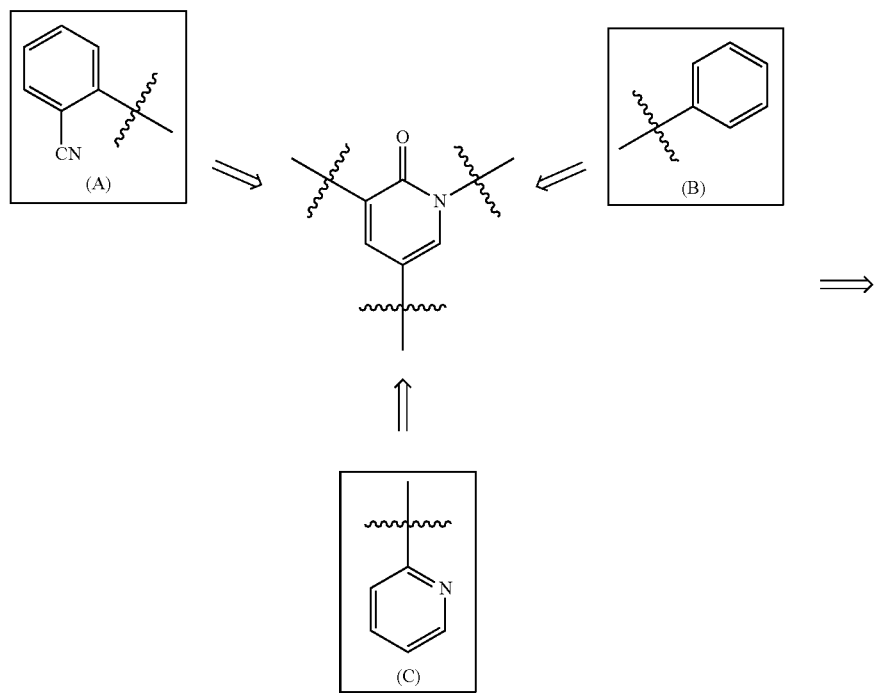

Scheme 1

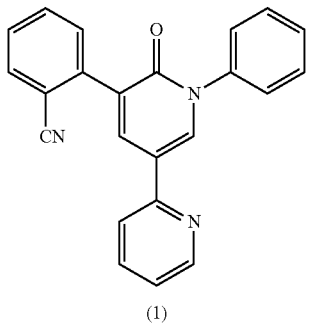

EP1300396 describes a process for preparing Perampanel by sequential combination of the 1,2-dihydro-pyridin-2-one core with fragments (B), (A) and (C). Example 7 discloses a process for producing Perampanel by reacting 3-(2-cyanophenyl)-5-(2-pyridyl)-2(1H)-pyridone with phenyl boronic acid, copper acetate and triethylamine in methylene chloride, followed by addition of concentrated aqueous ammonia, water and ethyl acetate.

WO 03/047577 discloses a process for preparing Perampanel by sequential coupling of the 1,2-dihydro-pyridin-2-one core with fragments (C), (A) and (B).

WO 2007/072868 and U.S. Pat. No. 7,524,967 describe a process for preparing Perampanel by combination of the 1,2-dihydropyridin-2-one core with fragments (C), (B) and (A). In this process, commercially available 2-methoxypyridine is brominated to 5-bromo-2-methoxypyridine, which is transformed to 6-methoxy-3,2'-bipyridine by reaction with n-butyllithium and 2-benzenesulfonylpyridine. Acid hydrolysis of the resulting 6-methoxy-3,2'-bipyridine gives a key intermediate—5-(2'-pyridyl)-2-pyridone (U.S. Pat. No. 7,524,967). Coupling of this compound with triphenylboroxine in the presence of copper acetate, pyridine and N,N-dimethylformamide yields 5-(2-pyridyl)-1-phenyl-1,2-dihydropyridine-2-one, which is brominated with NBS and coupled with 2-(1,3,2-dioxaborinan-2-yl)benzonitrile in the presence of palladium acetate, triphenylphosphine and potassium carbonate in 1,2-dimethoxyethane (Scheme 2) (WO 2007/072868).

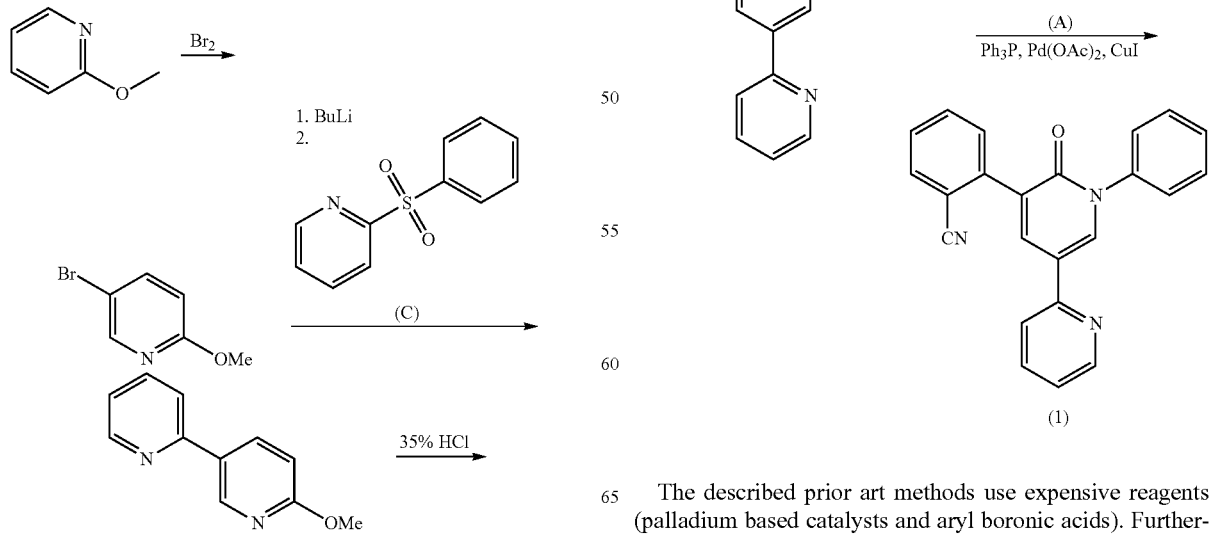

The described prior art methods use expensive reagents (palladium based catalysts and aryl boronic acids). Furthermore, palladium catalysts are used in homogeneous catalysis, which requires the step of palladium capture by post-treatment of the drug intermediate with a special absorbent, for example, by modified silica. Additional purification methods under special analytical control are used for removing traces of heavy metals (copper and palladium) from the intermediates and the final product, which increases the production cost and decreases its effectiveness.

Therefore, there continues to be a need in the art for a practical method, which does not employ heavy metals, for making Perampanel, a method that not only avoids the problems of the existing art, but is also safe, cost effective, and industrially feasible.

SUMMARY OF THE INVENTION

The present invention describes a process for the synthesis of 3-(2-cyanophenyl)-5-(2-pyridyl)-1-phenyl-1,2-dihydro-pyridin-2-one (Perampanel) represented by the structure of formula (1), and salts thereof, especially salts with pharmaceutically acceptable acids. The present invention further relates to certain intermediates formed and/or used in such process.

The process for manufacturing Perampanel (1) according to the present invention comprises the following steps:

a). reacting a compound of formula (2) with a formylating agent to form a compound of formula (3):

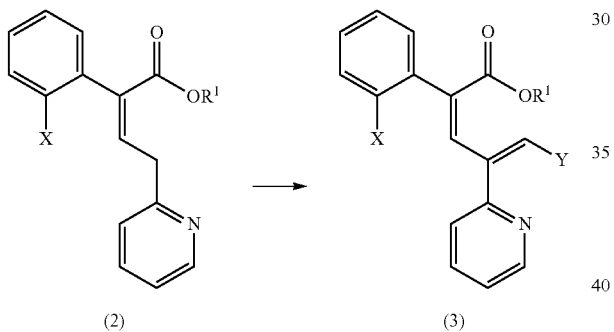

wherein

Y is $OR^2$ or $NR^3R^4$;

$R^1$, $R^2$, $R^3$ and $R^4$ are each independently a (C1-C4)-alkyl or an aryl; and X is a group that can be converted to a CN group;

b). reacting compound (3) with aniline to form a compound of formula (4):

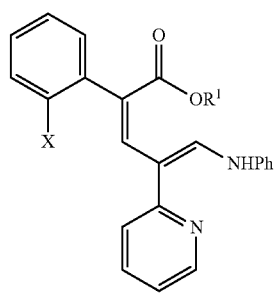

c). cyclizing the compound of formula (4) to form a compound of formula (5):

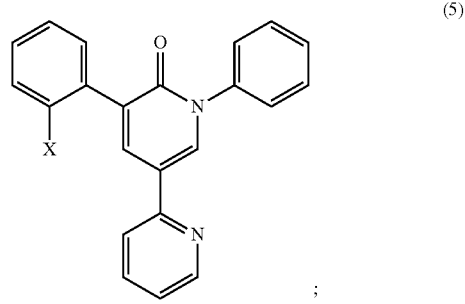

and d). converting compound (5) to 3-(2-cyanophenyl)-5-(2-pyridyl)-1-phenyl-1,2-dihydropyridin-2-one (1) (Perampanel)

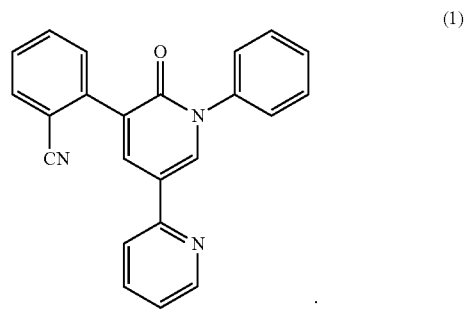

The process is schematically depicted in Scheme 3 hereinbelow.

In one embodiment, the group X is selected from the group consisting of halogen, acetal, —C(=O)H, —C(=N)—OH, C(=O)NH$_2$, sulfonyloxy, NHZ$^1$ wherein Z is a H or a nitrogen protecting group, and OZ$^2$ wherein Z$^2$ is H or a hydroxy protecting group. In another embodiment, X is a sulfonyloxy selected from the group consisting of mesylate (Ms), tosylate (Ts) and triflate (Tf). In other embodiments, X is an acetal represented by the structure CH(OR$^5$)$_2$ wherein each R$^5$ is independently a C1-C4 alkyl or CH(OR$^5$)$_2$ represents a cyclic acetal. According to a currently preferred embodiment, X is 1,3-dioxane or 1,3-dioxolane. Each possibility represents a separate embodiment of the present invention.

In some embodiments, the formylating agent in step (a) is selected from the group consisting of an alkyl formate, trialkyl orthoformate and a formamidedialkylacetal derivative. Each possibility represents a separate embodiment of the present invention.

In one particular embodiment, $R^1$ is methyl or ethyl and $R^2$ is methyl.

In one embodiment, Y in compound (3) is $OR^1$, and the process comprises the following steps:

a). reacting a compound of formula (2) with a formylating agent selected from an alkyl formate and a trialkyl orthoformate to form a compound of formula (6);

b). reacting compound (6) with aniline to form a compound of formula (7);

c). cyclizing the compound of formula (7) to a compound of formula (5); and d). converting of compound (5) to Perampanel (1).

The process is schematically depicted in Scheme 4 hereinbelow.

In one embodiment, compound (2) can be converted directly to compound (6) by reaction with a trialkyl orthoformate. In another embodiment, compound (2) can first be converted into an intermediate compound having an alcohol functionality, which is then alkylated to give a compound of formula (6). In accordance with this embodiment, the formylating agent is an alkyl formate, and step (a) comprises the following steps:

(i) reacting a compound of formula (2) with an alkyl formate in the presence of a lewis acid so as to form an intermediate compound having an alcohol functionality:

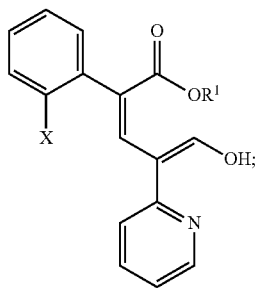

and (ii) alkylating the product obtained in step (i) with an alkylating agent in the presence of a base so as to form a compound of formula (6).

In other embodiments, Y in compound (2) is $NR^3R^4$ and the process comprises the following steps:

a). reacting a compound of formula (2) with a formamidedialkylacetal derivative to form a compound of formula (8);

b). reacting compound of formula (8) with aniline to form a compound of formula (7);

c). cyclizing the compound of formula (7) to form compound of formula (5); and d). converting compound (5) to Perampanel (1).

The process is schematically depicted in Scheme 6 hereinbelow.

In yet another embodiment, Y is $NR^3R^4$ and the process further comprises the following steps:

a). reacting a compound of formula (2) with a formamidedialkylacetal derivative to form a compound of formula (8);

b1). reacting compound of formula (8) with an alcohol of formula $R^2OH$ to form a compound of formula (6);

b2). reacting compound of formula (6) with aniline to form a compound of formula (7);

c). cyclizing the compound of formula (7) to form compound of formula (5); and d). converting compound (5) to Perampanel (1).

The process is schematically depicted in Scheme 7 hereinbelow.

In some embodiments, Y is $NR^3R^4$ and the formamidedialkylacetal derivative is dimethylformamide dimethyl acetal (DMF-DMA).

In one particular embodiment, $R^1$, $R^2$, $R^3$ and $R^4$ are each methyl or ethyl.

In some embodiments, steps (b) and (c) are carried out as a single step by mixing compound (3) with aniline under heat resulting in a compound of formula (5).

In one currently preferred embodiment, X in compound (5) is an acetal represented by the structure $CH(OR^5)_2$ wherein each $R^5$ is a C1-C4 alkyl, or $CH(OR^5)_2$ is cyclic acetal such as 1,3-dioxane or 1,3-dioxolane. In accordance with this embodiment, step (d) of the process of the invention comprises the following steps:

(i) converting the acetal group of compound (5) to the corresponding aldehyde (X=CHO);

(ii). reacting the aldehyde obtained in step (i) with hydroxylamine to form an oxime (X is CH=N—OH); and (iii). dehydrating the oxime formed in step (ii) to compound (1) (X is CN) in the presence of dehydration agent.

In one embodiment, in step (i) deprotection of the acetal group of compound (5) to the corresponding aldehyde (X=CHO) is performed by acid catalyzed transacetalization in acetone or hydrolysis in wet solvents or in aqueous acid, or under neutral conditions in the presence of a catalytic amount of iodine.

In another embodiment, in step (iii) the dehydration agent is selected from the group consisting of phosphorous oxychloride, thionyl chloride, triphosgene, propylphosphonic anhydride, ethyl dichlorophosphate, methanesulfonyl chloride, 2,4,6-trichloro-[1,3,5]triazine in N,N-dimethylformamide, chloral, Burgess reagent (methyl N-(triethylammonium-sulfonyl)carbamate), inorganic and organic acid anhydrides.

The present invention further provides a process for the preparation of the starting material of formula (2), comprising the step of reacting a phosphonium salt of formula (11) with a compound of formula (12) in the presence of a base:

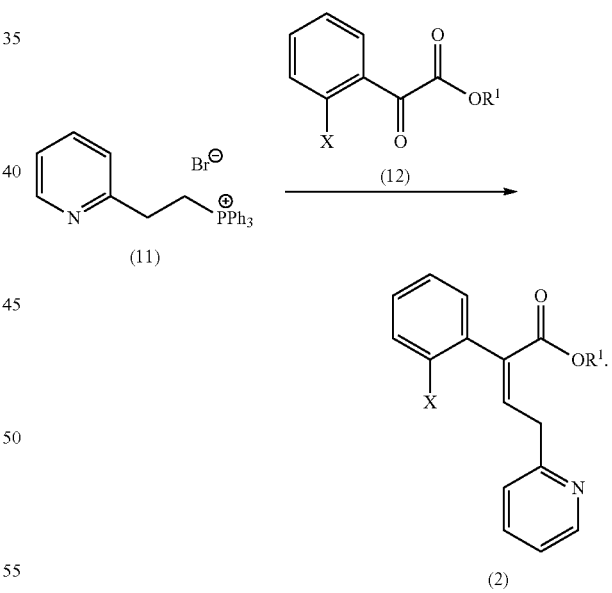

In other embodiments, the present invention further relates to intermediate compounds formed in the processes described herein, and use of such compounds (e.g., compound (5) as intermediates in a process for preparing Perampanel. Thus, in one embodiment, the present invention relates to the compound 3-(2-X-phenyl)-5-(2-pyridyl)-1-phenyl-1,2-dihydropyridin-2-one (5), wherein X is each group, which can be converted to CN group, such as halogen, acetal, —C(=O)H, —C(=N)—OH, C(=O)NH$_2$, sulfonyloxy, NHZ$^1$ wherein Z is H or a nitrogen protecting group, and $OZ^2$ wherein $Z^2$ is H or a hydroxy protecting group. Each possibility represents a separate embodiment of the present invention.

In some embodiments, the processes of the present invention further comprise the step of converting Perampanel to a pharmaceutically acceptable salt thereof, preferably a salt with a pharmaceutically acceptable acid.

In some embodiments, the present invention further provides a method of treating or preventing epilepsy or seizures, comprising the step of administering to a subject in need thereof an effective amount of the Perampanel which is produced in accordance with the process of the present invention, or a pharmaceutical composition comprising such compound.

In additional embodiments, the present invention provides the use of an effective amount of the Perampanel which is manufactured in accordance with the process of the present invention, or a pharmaceutical composition comprising such compound, for the manufacture of a medicament for treating epilepsy or seizures.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention relates to processes for the synthesis and isolation of the 3-(2-cyanophenyl)-5-(2-pyridyl)-1-phenyl-1,2-dihydropyridin-2-one (Perampanel), which avoid the use of palladium catalysts. Generally, the present invention can be accomplished in accordance with a few general alternative embodiments as described herein.

More specific reference to each of such alternative embodiments will now be made. It is apparent to a person of skill in the art, however, that any description provided herein is exemplary in nature and should not be construed as limiting the broad scope of the present invention.

Chemical Definitions:

The term "C1-C4 alkyl" as used herein alone or as part of another group refers to any saturated aliphatic hydrocarbon, including straight-chain, and branched-chain which contains 1 to 4 carbon atoms. Examples of C1-C4 alkyl groups include methyl, ethyl, n-propyl, isopropyl, n-butyl, sec-butyl, isobutyl and t-butyl. The C1-C4 alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. Each possibility represents a separate embodiment of the present invention.

The term "aryl" as used herein alone or as part of another group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "hydroxy-protecting group" as used herein alone or as part of another group refers to a readily cleavable group bonded to hydroxyl groups. The nature of the hydroxy-protecting groups is not critical so long as the derivatized hydroxyl group is stable. An example of a hydroxy protecting group is a silyl group, which can be substituted with alkyl (trialkylsilyl), with an aryl (triarylsilyl) or a combination thereof (e.g., dialkylphenylsilyl). Non-limiting examples of a silyl protecting group are trimethylsilyl (TMS), triethylsilyl (TES), t-butyldimethylsilyl (TBDMS), t-butyldiphenylsilyl (TBDPS), tripropylsilyl, triisopropylsilyl, triphenylsilyl, and the like. Other examples of hydroxy protecting groups include, for example, $C_1$-$C_4$ alkyl, $C_1$-$C_4$ alkyl-O—$C_1$-$C_4$ alkyl, $C_1$-$C_4$ alkyl-O—$C_1$-$C_4$ alkylaryl, $C_1$-$C_4$ alkyl-O-aryl, —CO—($C_1$-$C_6$ alkyl), —$SO_2$—($C_1$-$C_6$ alkyl), —$SO_2$-aryl, —CO-aryl, and —CO—($C_1$-$C_6$ alkyl)Ar (e.g., a carboxybenzyl group). Specific examples include but are not limited to methoxymethyl, benzyloxymethyl, methoxyethoxymethyl, ethoxymethyl, tetrahydropyranyl, t-butyl, 4-methoxybenzy, acetate (Ac), benzyl (Bzl), tetrahydropyranyl (THP), trityl (Trt) and the like.

The term "amino-protecting group" or "nitrogen protecting group" as used herein interchangeably alone or as part of another group refers to a readily cleavable group bonded to amine groups. Examples of nitrogen protecting groups include t-butoxycarbonyl (BOC), Fluorenylmethyloxycarbony (F-moc), benzyloxycarbonyl, acetyl, phenylcarbonyl, or a silyl group, which can be substituted with alkyl (trialkylsilyl), with an aryl (triarylsilyl) or a combination thereof (e.g., dialkylphenylsilyl), e.g., trimethylsilyl (TMS) or t-butyldimethyl silyl (TBDMS).

Other examples of hydroxy-protecting groups and nitrogen protecting groups, as well as their methods of incorporation and deprotection, are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in OrganicSynthesis," 2nd ed., John Wiley and Sons, New York, N.Y., 1991 and A. J. Pearson and W. R. Roush, Activating Agents and Protecting Groups, John Wiley and Sons (1999), the contents of each of which are incorporated by reference in their entirety.

The term "sulfonyloxy" as used herein refers to a group of the formula —$OSO_2R$ wherein R is alkyl, aryl or alkylaryl. Non-limiting examples of sulfonyloxy groups include mesylate ($CH_3SO_3$-Ms), tosylate ($CH_3C_6H_4SO_3$-Ts) and triflate ($CF_2SO_3$, Tf).

The term "acetal" as used herein refers to a group $CH(OR^5)_2$ wherein each $R^5$ is independently a C1-C4 alkyl, or wherein $CH(OR^5)_2$ represents cyclic acetal. Specific examples of acetal groups for use in the process of the present invention is 1,3-dioxane or 1,3-dioxolane. The acetal group can be deprotected to form an aldehyde group which can in turn be converted to a CN group as described herein.

Process for Preparing Perampanel

The process for manufacturing compound (1) comprises the following steps (Scheme 3):

a). reacting an alkyl or aryl 2-(2-X-phenyl)-4-(pyridin-2-yl)but-2-enoate (α,β-unsaturated ester of formula (2)) with a formylating agent to form a compound of formula (3);

b). reacting compound (3) with aniline to form an alkyl or aryl 2-(2-X-phenyl)-5-(phenylamino)-4-(pyridin-2-yl)penta-2,4-dienoate of formula (4);

c). cyclizing the alkyl or aryl 2-(2-X-phenyl)-5-(phenylamino)-4-(pyridin-2-yl)penta-2,4-dienoate of formula (4) to form compound (5); and d). converting 3-(2-X-phenyl)-5-(2-pyridyl)-1-phenyl-1,2-dihydropyridin-2-one (5) to 3-(2-cyanophenyl)-5-(2-pyridyl)-1-phenyl-1,2-dihydropyridin-2-one (1) (Perampanel).

Scheme 3

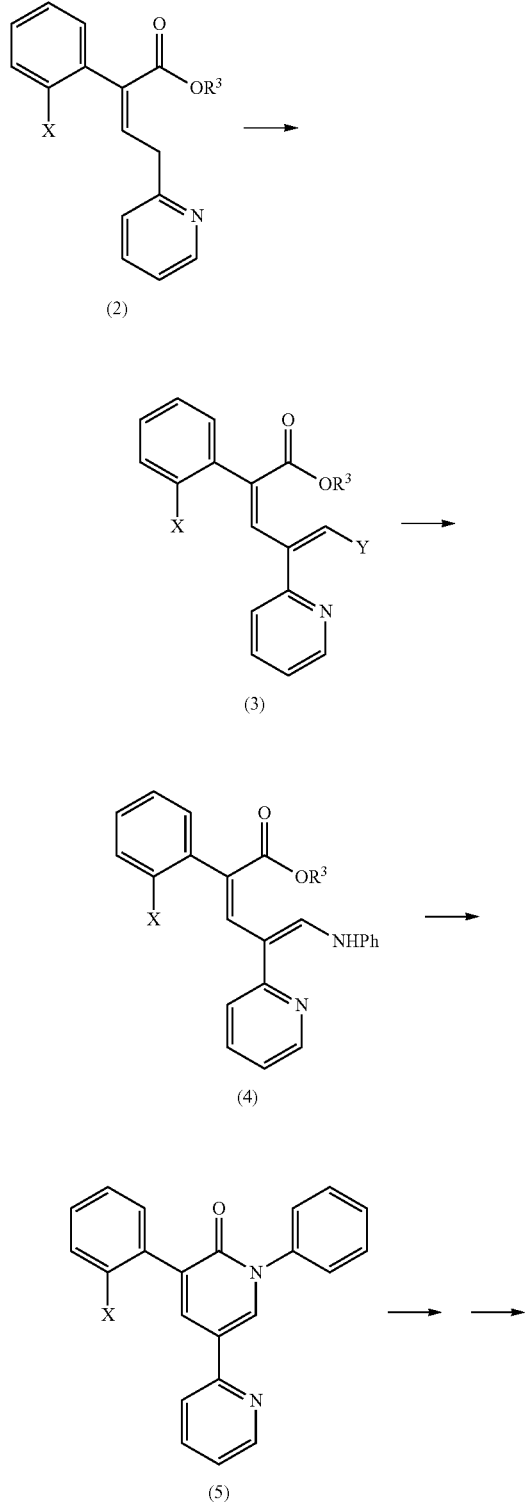

-continued

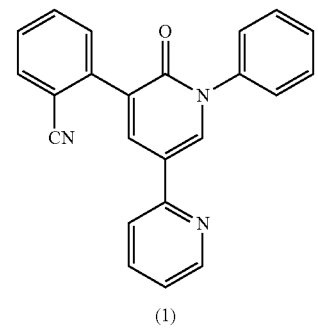 [SMILES: N#Cc1ccccc1-c1cc(-c2ccccn2)cn(-c2ccccc2)c1=O]

(1)

In Scheme 3, Y is $OR^2$ or $NR^3R^4$; $R^1$, $R^2$, $R^3$ and $R^4$ are each independently a (C1-C4)-alkyl or an aryl; and X is a group that can be converted to a CN group.

Surprisingly, it was found that when X=CN, the reaction proceeds with negligible yield of compound (3). The yields were increased significantly (65-70%) when X represents a functional group that can be converted to a CN group, e.g., halogen, acetal, —C(=O)H, —C(=N)—OH, C(=O)$NH_2$, sulfonyloxy (i.e., $OSO_2R$ wherein R is alkyl, alkylaryl or aryl), $NHZ^1$ wherein Z is H or a nitrogen protecting group (e.g., Ac), or $OZ^2$ wherein $Z^2$ is a H or hydroxy protecting group (e.g., Ac). In some embodiments, X is halogen, acetal, $NHZ^1$, OMs, OTs, OTf, OMe or $OZ^2$.

In some currently preferred embodiments, X is an acetal represented by the structure $CH(OR^5)_2$ wherein each $R^5$ is independently a C1-C4 alkyl, or wherein $CH(OR^5)_2$ represents cyclic acetal, preferably 1,3-dioxane or 1,3-dioxolane. In accordance with this embodiment, the acetal may be converted to a CN by (i) converting the acetal group of compound (5) to the corresponding aldehyde (X=CHO); (ii). reacting the aldehyde obtained in step (i) with hydroxylamine to form an oxime (X is CH=N—OH); and (iii)) dehydrating the oxime formed in step (ii) to compound (1) (X is CN) in the presence of dehydration agent.

In one embodiment, Y in compound (3) is $OR^2$, and the process comprises the following steps (Scheme 4):

a). reacting an alkyl or aryl 2-(2-X-phenyl)-4-(pyridin-2-yl)but-2-enoate of formula (2) with a formylating agent selected from an alkyl formate and trialkyl orthoformate to form an alkyl or aryl 2-(2-X-phenyl)-5-alkoxy-4-(pyridin-2-yl)penta-2,4-dienoate of formula (6);

b). reacting compound (6) with aniline to form an alkyl or aryl 2-(2-X-phenyl)-5-(phenylamino)-4-(pyridin-2-yl)penta-2,4-dienoate of formula (7);

c). cyclizing the alkyl or aryl 2-(2-X-phenyl)-5-(phenylamino)-4-(pyridin-2-yl)penta-2,4-dienoate of formula (7) to 3-(2-X-phenyl)-5-(2-pyridyl)-1-phenyl-1,2-dihydropyridin-2-one (5); and d). converting 3-(2-X-phenyl)-5-(2-pyridyl)-1-phenyl-1,2-dihydropyridin-2-one (5) to Perampanel (1).

Scheme 4

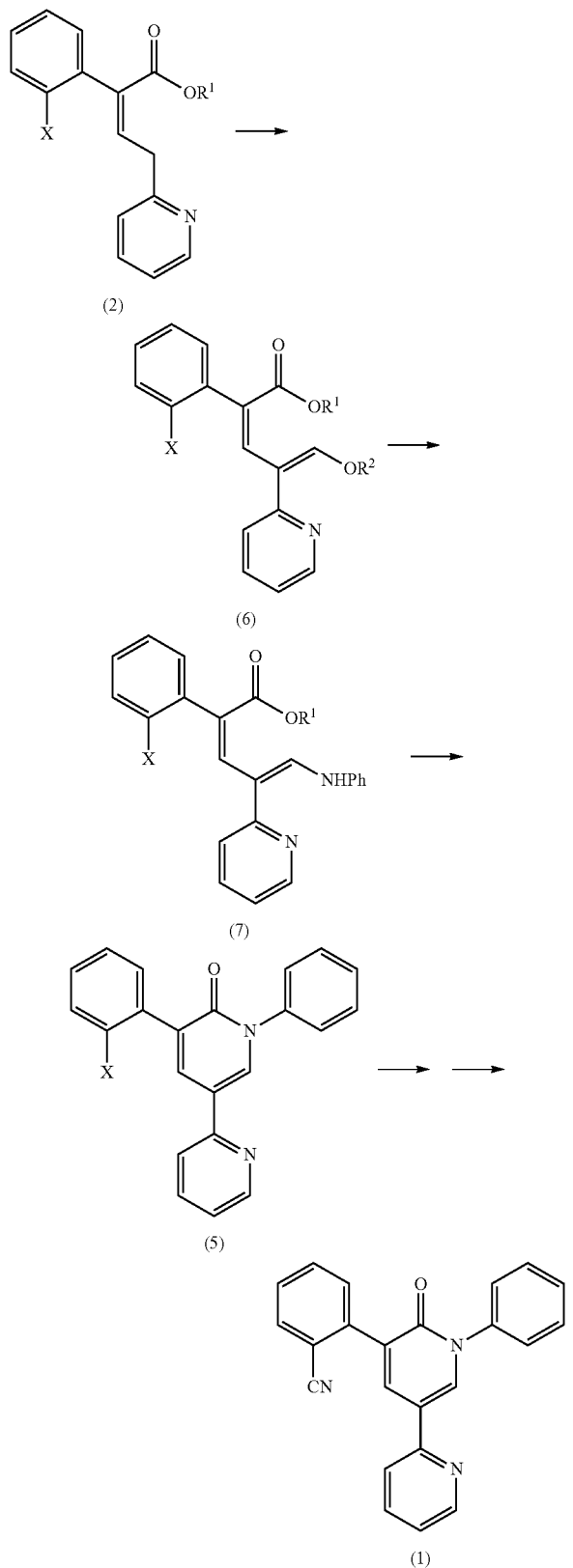

In one preferred embodiment, R¹ is methyl or ethyl, and R² is methyl, and the process is illustrated in Scheme 5:

Scheme 5

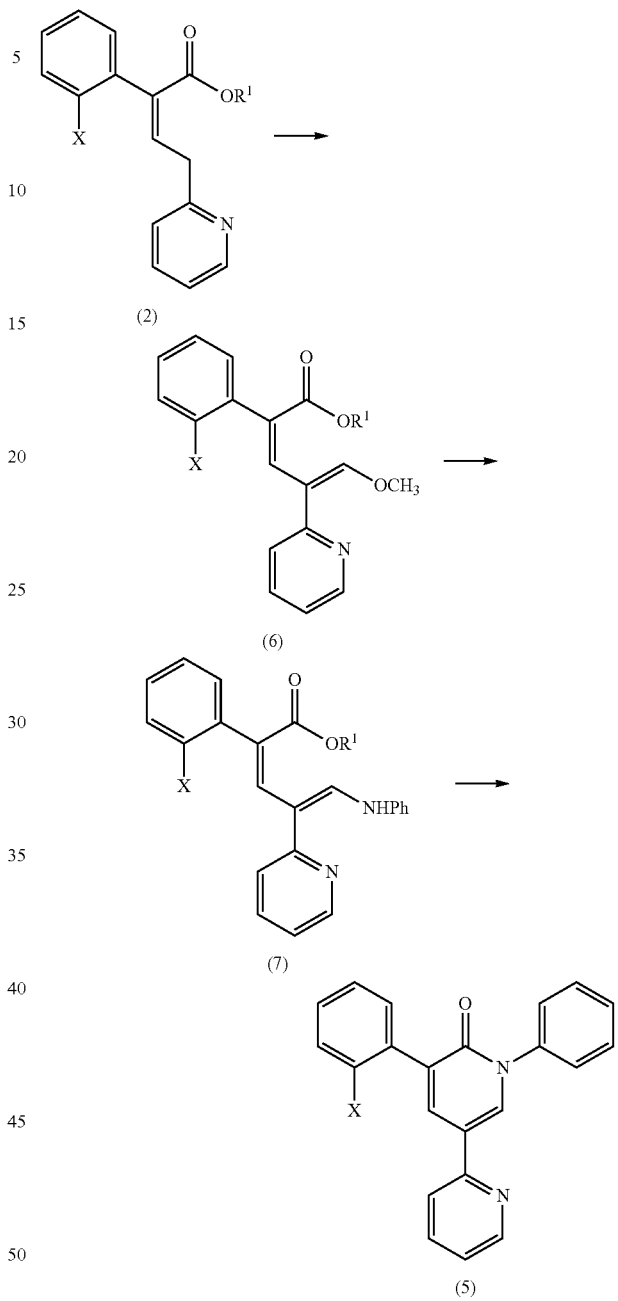

In some embodiments, compound (2) can be converted directly to compound (6) by reaction with an appropriate formylating agent, e.g. an orthoformate. Thus, in some embodiments, the process of the invention as illustrated in Schemes 4 and 5 comprises reaction of α,β-unsaturated ester (2) with an orthoformate, to form methoxymethylene derivative (6). The process is carried out, e.g., by mixing a tri-(alkyl) orthoformate, preferably triethyl or trimethyl-orthoformate, with α,β-unsaturated ester (2) and acetic anhydride in acetic acid as solvent or any other suitable solvent. After the exothermic reaction subsides, the reaction mixture is stirred at ambient temperature until completion of the reaction, as determined by, e.g., TLC analysis, to produce methoxymethylene derivative (6). The reaction is preferably carried out using an excess of the tri-(alkyl)orthoformate, preferably about 1.3 to 1.7 mole per mole of ester (5), and of the acetic anhydride, preferably about 2.0 to 3.0 mole per mole of ester (5). The resulting intermediate (6) can be used in the next step of the process without further purification or it can be isolated and further purified, with each possibility representing a separate embodiment of the present invention.

Alternatively, compound (2) can be converted to compound (6) by first preparing an intermediate compound having an alcohol (OH) functionality, and reacting the intermediate with an appropriate alkylating agent (e.g., a methylating agent). Thus, in some embodiments, the method for preparing a compound of general formula (6) according to the present invention comprises the steps of:

(1) conducting a formylation reaction by reacting a compound of general formula (2) with a formylating agent (e.g., an alkyl formate) in an aprotic solvent in the presence of a Lewis acid at a temperature ranging from −20° C. to 100° C., and adding an organic base to promote the reaction so that an intermediate product is obtained having an alcohol functionality:

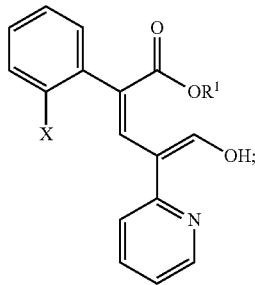

and 2) conducting an alkylation reaction (e.g., a methylation reaction) by reacting the intermediate product obtained in step (1) with a methylating agent in the presence of an alkali at a temperature ranging from about −20° C. to about 100° C. to obtain the compound of general formula (6).

In the aforementioned embodiment of the present invention, a compound of general formula (2) reacts with a formylating agent in an aprotic solvent in the presence of a Lewis acid at a temperature ranging from about −20° C. to about 100° C., preferably from about −10° C. to about 50° C., and more preferably from about −5° C. to about 10° C., under stirring. After a period of time, an organic base is added to promote the reaction during constant stirring. Then an organic acid such as formic acid or acetic acid, or an inorganic acid such as hydrochloric acid, phosphoric acid or sulfuric acid, is added in order to quench the reaction. The obtained intermediate product is separated from the mixture, and then reacts with a methylating agent in a medium suitable for methylation, in alkaline conditions at a temperature ranging from about −20° C. to about 100° C., preferably from about 10° C. to about 60° C. After the reaction is completed, the obtained compound of general formula (6) is separated from the mixture.

The Lewis acid used in said process generally refers to Lewis acid known to one skilled in the art, such as titanium tetrachloride, aluminum trichloride, tin chloride, ferric chloride, zinc chloride and boron trifluoride ethyl ether and the like, preferably titanium tetrachloride. Each possibility represents a separate embodiment of the present invention. The amount of the Lewis acid used is, for example, about 0.1 to about 6.0 molar equivalents, preferably about 1.0 to about 3.0 molar equivalents per 1.0 molar equivalent of the compound of general formula (2).

The formylating agent used in the process of the present invention includes formylating agents known to one skilled in the art. Non-limiting examples include trialkyl orthoformates (i.e., compounds of the formula $CH(OR)_3$ wherein R is alkyl), such as trimethyl orthoformate and triethyl orthoformate, or alkyl formates (i.e., compounds of the formula $CH(=O)R$ wherein R is alkyl), such as methyl formate or ethyl formate. In some currently preferred embodiment, the formylating agent is methyl formate or trimethyl orthoformate. Each possibility represents a separate embodiment of the present invention. The amount of the formylating agent used is, for example, from about 1.0 to about 10.0 molar equivalents, preferably from about 1.0 to about 3.0 molar equivalents per 1.00 molar equivalent of the compound of general formula (2).

The bases that may be used in the process of the present invention include, but are not limited to, organic bases such as amines, preferably tertiary amines like trimethyl amine, triethyl amine, tributyl amine, diisopropylethyl amine, pyridine and the like; and inorganic bases, such as sodium hydroxide, potassium hydroxide, sodium carbonate, potassium carbonate, sodium bicarbonate, potassium bicarbonate, sodium methoxide, sodium ethoxide and sodium tertiary-butoxide, preferably sodium hydroxide or potassium hydroxide. Each possibility represents a separate embodiment of the present invention. The amount of the base used is, for example, from about 1 to about 10.0 molar equivalents, preferably from about 2.0 to about 5.0 molar equivalents per 1.0 molar equivalent of the compound of general formula (2).

The methylating agent used in the present invention includes any methylating agents known to one skilled in the art, such as dimethyl sulfate, trimethyl orthoformate, chloromethane, bromomethane and iodomethane, and the like. In one currently preferred embodiment, the methylating agent is dimethyl sulfate. Each possibility represents a separate embodiment of the present invention. Other alkylating agents can be used in replacement of the methylating agent.

The formylation reaction is preferably conducted in an aprotic solvent, such as halogenated hydrocarbons, aromatic hydrocarbons, saturated hydrocarbons, dimethyl sulfoxide, etc., preferably halogenated hydrocarbon such as dichloroethane, dichloromethane, trichloromethane and chlorobenzene. Each possibility represents a separate embodiment of the present invention.

The medium suitable for conducting the methylation reaction may be a polar or a non-polar solvent, such as aromatic hydrocarbons (e.g., benzene, toluene), halogenated hydrocarbons (e.g., chlorobenzene, dichloromethane, dichloroethane), alcohols (e.g., methanol, ethanol, IPA), ethers (e.g., ethyl ether, 1,2-dimethoxyethane, tetrahydrofuran, dioxane), ketones (e.g., acetone, methyl ethyl ketone, methyl isobutyl ketone), esters (e.g., ethyl acetate, isopropyl acetate, and butyl acetate) and the like. Each possibility represents a separate embodiment of the present invention.

In another alternative embodiment of the process of the present invention, Y in compound (3) is $NR^3R^4$, and the process comprises the following steps (Scheme 6):

a). reacting a an alkyl or aryl 2-(2-X-phenyl)-4-(pyridin-2-yl)but-2-enoate of formula (2) with a formamidedialkylacetal derivative to form an alkyl or aryl 2-(2-X-phenyl)-5-dialkyl (or diaryl)-amino-4-(pyridin-2-yl)penta-2,4-dienoate of formula (8);

b). reacting compound (8) with aniline to form an alkyl or aryl 2-(2-X-phenyl)-5-(phenylamino)-4-(pyridin-2-yl)penta-2,4-dienoate of formula (7);

c). cyclizing the alkyl or aryl 2-(2-X-phenyl)-5-(phenylamino)-4-(pyridin-2-yl)penta-2,4-dienoate of formula (7) to 3-(2-X-phenyl)-5-(2-pyridyl)-1-phenyl-1,2-dihydropyridin-2-one (5); and d). converting 3-(2-X-phenyl)-5-(2-pyridyl)-1-phenyl-1,2-dihydropyridin-2-one (5) to Perampanel (1).

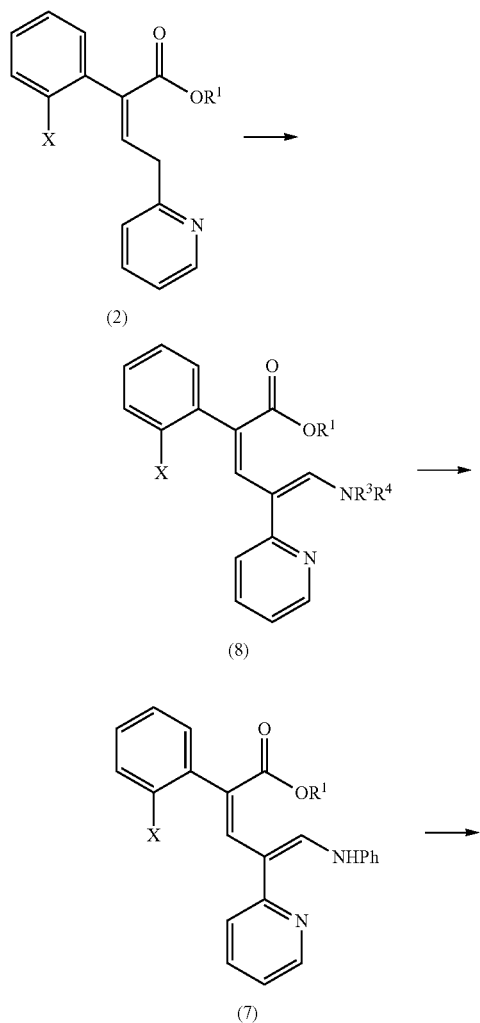

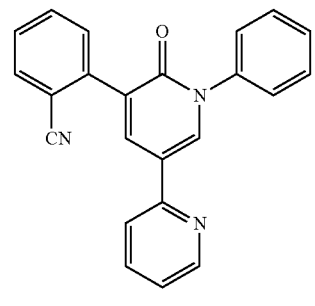

wherein X is as defined above and $R^1$, $R^3$ and $R^4$ are each independently a (C1-C4)-alkyl or an aryl.

In one embodiment of the aforementioned process, dialkylformamide dialkylacetals, preferably dimethyl formamide dimethylacetal (DMF-DMA) are used in the process of converting compound (2) to compound (8). Intermediate (8) may be converted directly to compound (7) by reacting compound (8) with aniline, or it may first be converted to compound (6) by reacting compound (8) with an alcohol. Compound (6) can be further reacted with aniline to form compound (7). These embodiments are illustrated in Scheme 7, with each possibility representing a separate embodiment of the present invention.

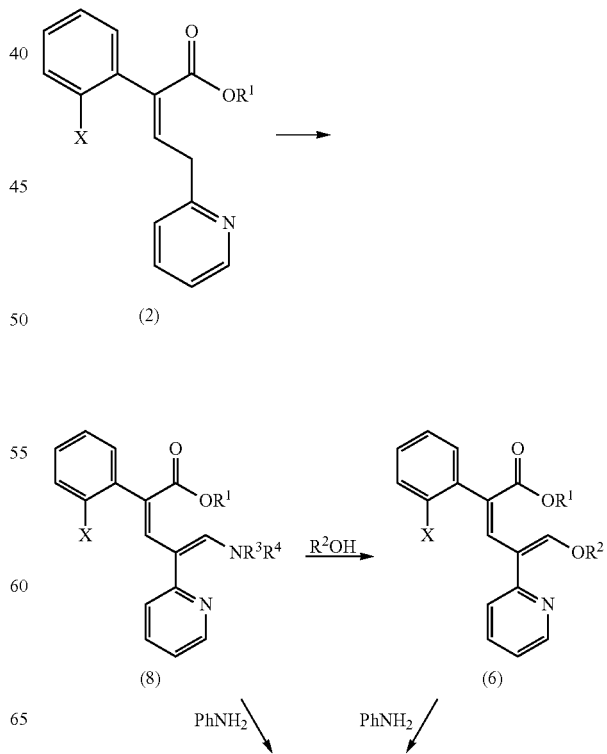

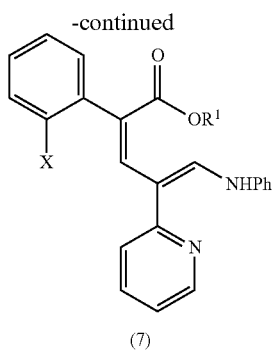

One specific embodiment is represented in Scheme 8:

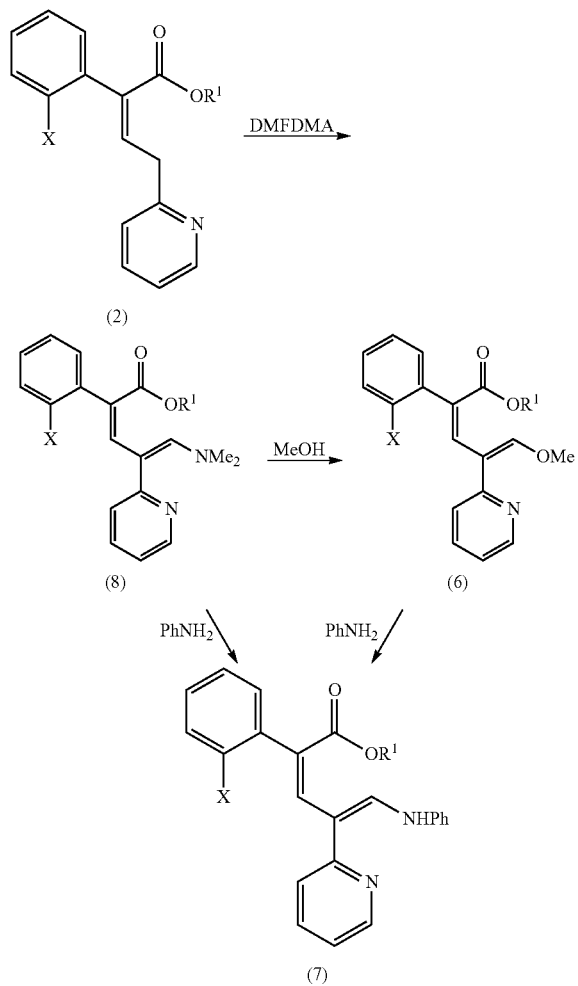

The reaction to obtain the enamine moiety is preferably conducted under conditions so as to keep the other functional groups in the molecule intact. The reaction is usually conducted under an inert atmosphere such as nitrogen or argon. The reaction can take place neat or in any inert solvent, preferably in an aprotic solvent such as halogenated hydrocarbons e.g. methylene chloride; ethers e.g. THF, TBME, or dioxane; or aromatic solvents such as benzene, chlorobenzene, toluene, phenylethane, and xylenes. Prefer-ably the solvent is toluene. The reaction duration and set temperature are chosen so as to bring the reaction to completion at a minimum time in order to avoid the production of unwanted side products. Typically the reaction can be conducted at about 0° C. to about reflux, preferably from about 20 to about 150° C., more preferably from about 60° C. to about 130° C. For example: from about 80° C. to about 110° C., for about 6 h to about 48 h, preferably from about 10 h to about 36 h, most preferably from about 12 h to about 24 h, such as from about 20 h to about 24 h.

The process of the invention comprising reaction of compound (6) with aniline is carried out in any inert solvent, preferably in THF. The resulting intermediate (7) can be used in the next step of the process without further purification or it can be isolated and further purified.

Alternatively, intermediate (7) can be prepared from enamine (8) by reaction with aniline. The reaction is carried out in an organic solvent, preferably, alcohols, such as methanol or ethanol in the presence of an organic acid such as formic acid, acetic acid and the like, or an inorganic acid such as hydrochloric acid, phosphoric acid, sulfuric acid and the like, preferably in the presence of hydrochloric acid, and acidic resins or insoluble in organic solvents inorganic acids such as molybdic acid. Each possibility represents a separate embodiment of the present invention.

Step (c) comprises cyclization of enamine (7) to form compound (5). The reaction is typically carried out in an organic solvent in the presence of basic catalysts. The bases used in the present invention include, but not limited to, organic bases, such as trimethyl amine, triethyl amine, tributyl amine, diisopropylethyl amine, pyridine, piperidine and the like; and inorganic bases such as sodium hydroxide, potassium hydroxide, sodium carbonate, potassium carbonate, sodium bicarbonate, potassium bicarbonate, sodium methoxide, sodium ethoxide and sodium tertiary butoxide, preferably, 1,8-diazabicyclo[5.4.0]undec-7-ene (DBU), 1,5-diazabicyclo[4.3.0]non-5-ene (DBN), 1,4-diazabicyclo[2.2.2]octane (DABCO), or phosphazene bases. Each possibility represents a separate embodiment of the present invention.

Alternatively, steps (b) and (c) can be carried out as a single step by mixing compound (3) (e.g., compounds (6) or (8)) with aniline and refluxing the mixture in an organic solvent, preferably ethanol, in the presence of a base catalyst or in DMF to bring the reaction to completion.

Preparation of Starting Materials α,β-Unsaturated ester (2) wherein R¹ is methyl or ethyl can be prepared by methods well known in art as illustrated in Scheme 9. Although the reactions in Scheme 9 exemplify the preparation of compound (2) as the methyl or ethyl ester (R¹=Me, Et), it is apparent to a person of skill in the art that other alkyl or aryl esters of formula (2) can be produced and used as intermediates in the process of the present invention, with each possibility representing a separate embodiment of the present invention.

Scheme 9

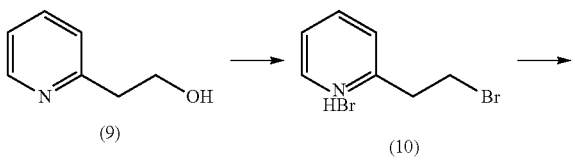

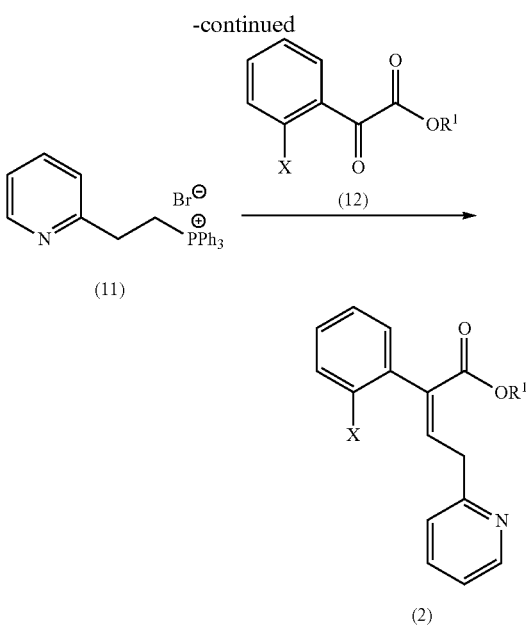

Transformation of hydroxy derivative (9) to its bromide (10) in the aforementioned process may be performed by any method well known in art (e.g., Larock R. C. Comprehensive Organic Transformations. A guide to functional group preparations. 2 ed., Wiley, 1999, p. 689-701), for example, by reaction with hydrobromic acid.

Quaternization of bromide (9) with triphenylphosphine may be performed according to methods, described in Science of Synthesis: Houben-Weyl Methods of Molecular Transformations Vol. 31b, Georg Thieme Verlag, May 14, 2014-Science, 2083-2090.

The reaction is typically carried in organic solvents, such as alcohols, acetonitrile, DMF, acetic acid, acetone or toluene and the like, preferably in toluene with heating.

Alternatively, phosphonium salt (11) may be prepared by reaction of hydroxy derivative (9) with triphenylphosphine hydrobromide (Zhang, J X et al. *Synthetic communications* (1996), vol. 26, iss. 16, pp. 3091-3095).

Methyl or ethyl 2-(2-X-phenyl)-2-oxoacetates (12) are commercially available compounds or can be prepared by any method well known in art, for example, ethyl 2-(2-(1,3-dioxolan-2-yl)phenyl)-2-oxoacetate can be prepared by reaction of (2-(1,3-dioxolan-2-yl)phenyl)magnesium bromide with diethyl oxalate (see Examples) or methyl 2-(2-Acetamidophenyl)-2-oxoacetate by reaction of N-acetylisatin with aminobenzoic ester in methanol (Ayman El-Faham et al. *Journal of Chemistry* Volume 2013, Article ID 901745, pages 1-6,).

The reaction of the phosphonium salt (11) with methyl or ethyl 2-(2-X-phenyl)-2-oxoacetates (12) to form α,β-unsaturated ester (2) is typically carried out in an organic solvent, preferably DMF, in the presence of a base. Examples of bases that may be used include but not limited to organic bases, such as 1,8-diazabicyclo[5.4.0]undec-7-ene (DBU), 1,5-diazabicyclo[4.3.0]non-5-ene (DBN), 1,4-diazabicyclo[2.2.2]octane (DABCO), phosphazene bases and like; butyl- and phenyl lithium; sodium and potassium amides, lithium diethylamide, lithium diisopropylamide, lithium piperidide, lithium, potassium and sodium bis(trimethylsilyl) amides; and metal alkoxides such as sodium methoxide, sodium ethoxide and potassium tertiary butoxide, preferably, potassium tert-butoxide. Alternatively, metal alkoxides can be prepared directly in the reaction mixture (in situ) by reaction of metal hydrides with the corresponding alcohols. Each possibility represents a separate embodiment of the present invention. A currently preferred base is potassium tert-butoxide (tert-BuOK).

Transformation of X-Group to Nitrile Group

Transformation of X-group of compound (5) to nitrile group of compound (1), i.e. transformation of 3-(2-X-phenyl)-5-(2-pyridyl)-1-phenyl-1,2-dihydropyridin-2-one (5) to Perampanel (1) in the aforementioned process (Schemes 3, 4 and 6) can be performed by any method well known in art. See, for example, Kim, J. et al. Synthesis of Aromatic Nitriles Using Nonmetallic Cyano-Group Sources. *Angewandte Chemie* International Edition, Volume 51, Issue 48, pages 11948-11959, Nov. 26, 2012:

X=Br by Rosenmund-von Braun Reaction, cyanation of aryl halides with an excess of copper(I) cyanide in a polar high-boiling solvent such as DMF, nitrobenzene, or pyridine at reflux temperature Zanon, J. et al. (*J. Am. Chem. Soc.*, 2003, 125, 2890-2891) or by reaction with $K_4[Fe(CN)_6]$ (a nontoxic cyanide source) in the presence of 0.1 mol % $Pd(OAc)_2$ (Weissman, S. A. et al. *J. Org. Chem.*, 2005, 70, 1508-1510; Grossman, O. et al, *Org. Lett.*, 2006, 8, 1189-1191)

X=Cl by reaction with $K_4[Fe(CN)_6]$ in the presence of a highly effective Pd catalyst (P. Y. Yeung, C. M. So, C. P. Lau, F. Y. Kwong, *Org. Lett.*, 2011, 13, 648-651; Cheng, Y et al. *Synlett*, 2007, 543-546; Liuke, A. et al., *Org. Lett.*, 2007, 9, 1711-1714).

X=$NH_2$ by Sandmeyer Reaction (via preparation of diazonium salt and subsequent displacement with a nucleophile (CN—).

X=CHO by the use of trichloroisocyanuric acid (TCCA) as an oxidant in aqueous ammonia (Veisi, H. *Synthesis*, 2010, 2631-2635) or by transformation into aldoxime following by its dehydration, using propylphosphonic anhydride (Augustine, J. K. et al. *Synlett*, 2009, 3378-3382), ethyl dichlorophosphate (Zhu, J. L. et al. *Synlett*, 2007, 1317-1319), methanesulfonyl chloride (Shargi H. et al. Synthesis, 2003, 243-246), 2,4,6-trichloro[1,3,5]triazine in N,N-dimethylformamide (De Luca, L et al. *J. Org. Chem.*, 2002, 67, 6272-6274), chloral (Chandrasekhar, S. et al. *Tetrahedron Lett.*, 2003, 44, 755-756) and other reagents (Larock R. C. Comprehensive Organic Transformations. A guide to functional group preparations. 2 ed., Wiley, 1999, p. 1659-1660).

X=$C(O)NH_2$ by the dehydration with $SOCl_2$, TsCl/pyridine, $P_2O_5$, $COCl_2$, $(EtO)_3P/I_2$, or $Ph_3P/CCl_4$ (Comprehensive Organic Transformations; Larock, R. C. Ed.; VCH: Weinheim, 1989, 976-993), using silanes in the presence of catalytic amounts of fluoride (Zhou, S. et al. *Org. Lett.*, 2009, 11, 2461-2464).

X=OMs, OTs by reaction with $K_4[Fe(CN)_6]$ in the presence of $Pd(OAc)_2$ catalyst and CMPos ligand (Yeung, P. Y. et al. *Angewandte Chemie* International Edition, Volume 49, Issue 47, pages 8918-8922, Nov. 15, 2010).

The contents of each reference cited herein is hereby incorporated by references in its entirety as if fully set forth herein.

The following examples will further illustrate the invention without, however, limiting it thereto.

EXAMPLES

Specific compounds which are representative of this invention were prepared as per the following examples and reaction sequences; the examples and the figures depicting the reaction sequences are offered by way of illustration, to aid in the understanding of the invention and should not be construed to limit in any way the invention set forth in the claims which follow thereafter.

No attempt has been made to optimize the yields obtained in any of the reactions. Unless otherwise noted, the materials used in the examples were obtained from readily available commercial suppliers or synthesized by standard methods known to one skilled in the art of chemical synthesis.

Example 1

Preparation of Compound (11):

Aqueous HBr (2.5 L) was charged into a clean and dry round bottom flask followed by compound (9) (250 g, 2.03 mol) and heated to 120° C. with azeotropical removal of water (~24 h). The residual water was removed by co-distillation with toluene (2×2 L), the solid was stirred in MTBE: IPA (1:1) for 1 h and filtered, washed with MTBE (200 ml) and dried in vacuum, yielding 360 g (66%) of light pink solid (compound (10)).

Water (750 ml) and compound (10) (180 g, 0.67 mole) were cooled to 10° C. Then the pH was adjusted to 9 using 3 N NaOH (650 ml), and the aqueous layer was extracted with dichloromethane (DCM, 2×200 ml). The organic layer was washed with water (2×200 ml), dried over Na$_2$SO$_4$ and filtered, diluted with 700 ml of toluene and the DCM was evaporated at 60° C. After distillation of DCM, 700 ml of toluene was added and cooled to RT. Then triphenylphosphine (TPP) (176.5 g, 0.67 mol) was added and the temperature was raised to 120° C. for 14 hr, and then cooled down. The solid was filtered off and dried at 70° C. in vacuum. 171 g (51%) of compound (11) was received as a white solid.

Preparation of 2-(2-(1,3-dioxolan-2-yl)phenyl)-2-oxoacetate (compound (12), X is

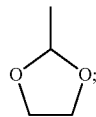

R$^1$ is ethyl)

(i) Preparation of 2-(2-bromophenyl)-1,3-dioxolane

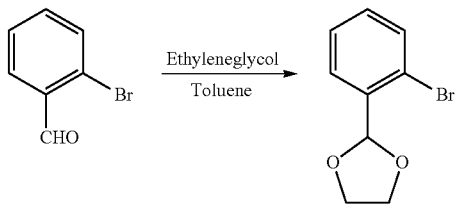 [SMILES: O=Cc1ccccc1Br ; Brc1ccccc1C1OCCO1]

Toluene (1 L), 2-bromobenzaldehyde (190 g, 1.05 mole) and ethylene glycol (76 ml, 1.3 mole) were heated to reflux with azeotropical distillation of water (~10 h). 600 ml of toluene was distilled off and the residual solution was cooled to RT and washed with sat. NaHCO$_3$ solution (200 ml), water (200 ml), dried over Na$_2$SO$_4$, and evaporated under reduced pressure. The crude compound was distilled under high vacuum. 190 g (82%) of 2-(2-bromophenyl)-1,3-dioxolane as a colorless liquid was received, purity by GC: 98%.

ii) Preparation of ethyl 2-(2-(1,3-dioxolan-2-yl)phenyl)-2-oxoacetate

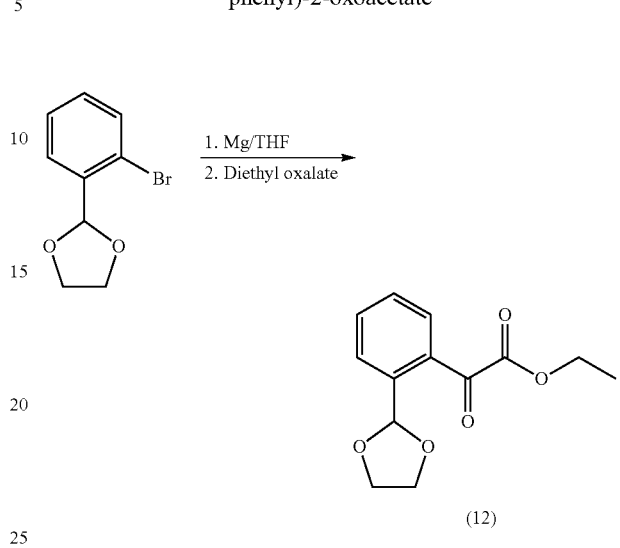

A few drops of 2-(2-bromophenyl)-1,3-dioxolane (0.2 g), catalytic amount of 12 and a few drops of 1,2 dibromoethane (for reaction initiation) were added into a Mg metal (3.2 g, 0.134 mol) suspension in THF (8 ml). 2-(2-bromophenyl)-1,3-dioxolane (24 g, 0.1 mole) in THF (100 ml) was added dropwise (40 min) into the reaction mixture. (exothermic reaction was detected 30-65° C.). After the dropwise addition, the reaction mixture was refluxed for 1 h, and cooled to RT.

Diethyl oxalate (29 g, 0.19 mol) in toluene (100 ml) was cooled to 0° C. and added dropwise to the above Grignard reagent in 35 min. at −5 to 0° C. The reaction mixture was stirred at 0° C. for 1 h. 7 ml of HCl in 70 ml of water was added to achieve pH=6-7. The aqueous layer was extracted with ethyl acetate (2×100 ml) and the organic solution was washed with 20% solution of NaHCO$_3$, brine (100 ml) and dried over Na$_2$SO$_4$. The solvent was evaporated under reduced pressure. Analytically pure sample was prepared by column chromatography, yielding ethyl 2-(2-(1,3-dioxolan-2-yl)phenyl)-2-oxoacetate as a solid with low melting point.

Preparation of compound (2) (X is

R$^1$ is ethyl)

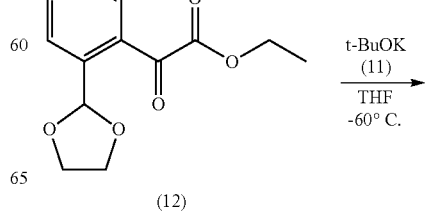

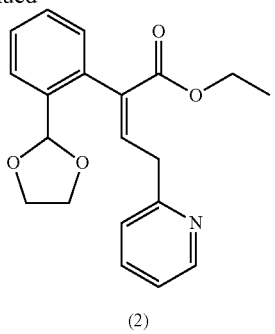

(2)

THF (50 ml) and phosphonium bromide (11) (4.2 g, 0.0096 mole) were cooled to −60° C. Potassium tert-butoxide (2.68 g, 0.024 mole) was added at −60° C. The reaction mixture was stirred at −60° C. for 10 min (yellow suspension was observed) and ethyl 2-(2-(1,3-dioxolan-2-yl)phenyl)-2-oxoacetate (3 g in 15 ml of THF, 0.12 mol) was added dropwise in 10 min at −60° C. Then, the reaction mixture was stirred at the same temperature for 40 min., and quenched with sat. NH₄Cl sol. (15 ml) at −40° C. The resulting reaction mixture was diluted with water (50 ml) and extracted with EtOAc (2×50 ml). Combined organic layers were washed with water, dried over Na₂SO₄ and transferred to the next step.

Preparation of Compound (8) (X is

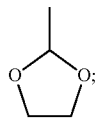

R¹ is ethyl; R³ and R³ and R⁴ are each methyl)

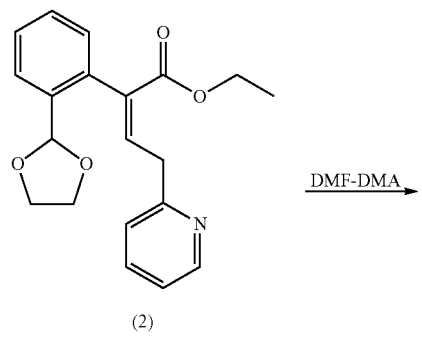

Toluene (20 ml) was added to ethyl acetate solution, containing 1.2 g (0.0035 mol) of compound (2). Ethyl acetate was distilled off and N,N-dimethylformamide dimethyl acetal (DMF-DMA) (1.26 g, 0.0106 mol) was added. The mixture was refluxed for 10 h. (The end of reaction was monitored by LCMS). The excess DMF-DMA and toluene were distilled out and the crude material was used without isolation in next step.

Preparation of Compound (5) (X=

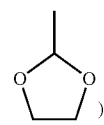
)

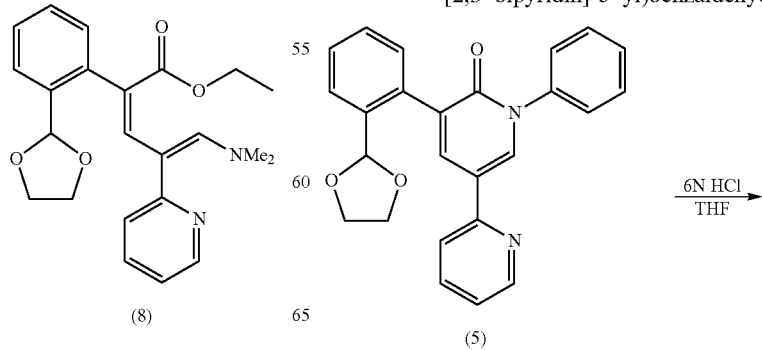

Compound (8) (1 g, 0.0025 mol), DBU (1.14 g, 0.0075 mole) and aniline (0.35 g, 0.0035 mole) were added to toluene (20 ml at RT). The reaction mixture was refluxed for 8 h (the end of reaction was monitored by LCMS). Toluene was distilled off. The crude material (1.6 g) was used without isolation in next step.

Conversion of Dioxolane Group to Nitrile Group

1) Preparation of 2-(6'-oxo-1'-phenyl-1',6'-dihydro-[2,3'-bipyridin]-5'-yl)benzaldehyde

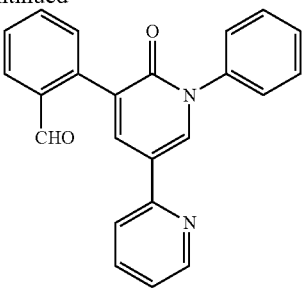

To THF (20 ml) containing compound (5) (1.6 g), 6N HCl (10 ml) was added and the reaction mixture was heated to 60° C. for 30 min. The reaction was monitored by TLC. THF was removed and the pH was adjusted to 7-8, using NaHCO₃, then residue was diluted with water (20 ml) and extracted with EtOAc (2×20 ml), dried over Na₂SO₄ and evaporated under reduced pressure. The obtained crude compound was stirred in 5 ml of MTBE, filtered and dried in vacuum. 2-(6'-oxo-1'-phenyl-1',6'-dihydro-[2,3'-bipyridin]-5'-yl)benzaldehyde obtained as a dark solid and was transferred to the next step without purification.

2) Preparation of 2-(6'-oxo-1'-phenyl-1',6'-dihydro-[2,3'-bipyridin]-5'-yl)benzaldehyde oxime

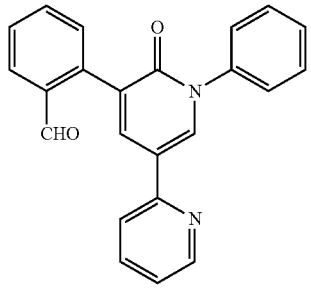

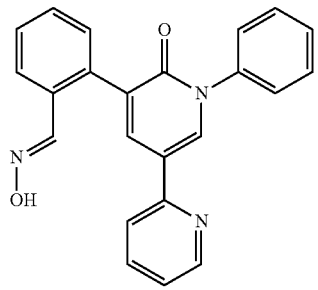

DMSO (5 ml), 2-(6'-oxo-1'-phenyl-1',6'-dihydro-[2,3'-bipyridin]-5'-yl)benzaldehyde (200 mg, 0.56 mol) and hydroxylamine hydrochloride (72 mg, 1 m mole) were heated to 60° C. for 30 min Reaction mixture was cooled to RT and diluted with water and extracted with ethyl acetate (2×20 ml). The organic solution was washed with water (2×25 ml), dried over Na₂SO₄ and evaporated under reduced pressure. The obtained crude was purified by column chromatography, yielding 150 mg (70%) of oxime as a light yellow solid.

3) Preparation of Perampanel

Ethylene dichloride (EDC) (10 ml) and 2-(6'-oxo-1'-phenyl-1',6'-dihydro-[2,3'-bipyridin]-5'-yl)benzaldehyde oxime (0.15 g, 0.0005 mole) were cooled to 10° C., then POCl₃ (0.1 ml, 0.00108 mol) was added. The reaction mixture was heated to 70° C. for 1 h. Reaction mass was cooled to RT, diluted with water (20 ml) and the pH was adjusted to 8 using NaHCO₃. Aqueous layer was extracted with DCM (2×20 ml), combined organic layers were washed with water, dried over Na₂SO₄ and evaporated under reduced pressure.

The obtained light yellow color solid was recrystallized according to any of the methods described in WO 2013/102897 to afford pure Perampanel.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A process for the preparation of 3-(2-cyanophenyl)-5-(2-pyridyl)-1-phenyl-1,2 dihydro-pyridin-2-one (Perampanel) represented by the structure of formula (1), and salts thereof,

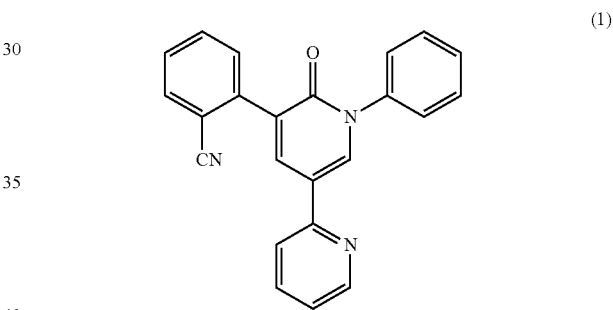

comprising the following steps:

a). reacting a compound of formula (2) with a formylating agent to form a compound of formula (3)

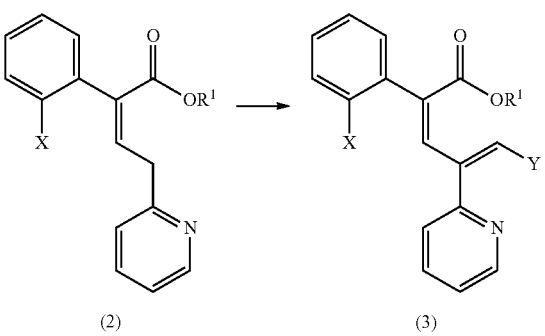

wherein

Y is OR² or NR³R⁴;

R¹, R², R³ and R⁴ are each independently a (C1-C4)-alkyl or an aryl; and

X is a group that can be converted to a CN group;

b). reacting compound (3) with aniline to form a compound of formula (4):

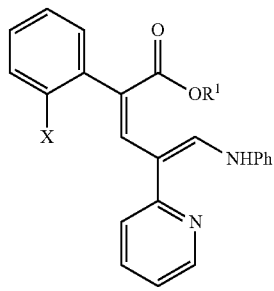
(4)

c). cyclizing the compound of formula (4) to form a compound of formula (5):

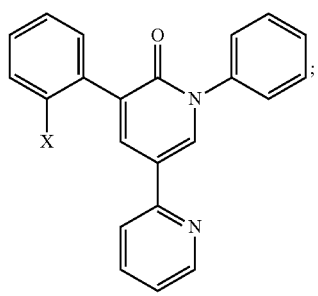
(5)

and d). converting compound (5) to 3-(2-cyanophenyl)-5-(2-pyridyl)-1-phenyl-1,2-dihydropyridin-2-one (1) (Perampanel).

2. The process according to claim 1, wherein X is selected from the group consisting of halogen, acetal, —C(=O)H, —C(=N)—OH, —C(=O)NH$_2$, sulfonyloxy, NHZ$^1$ wherein Z$^1$ is H or a nitrogen protecting group, and OZ$^2$ wherein Z$^2$ is a H or a hydroxy protecting group.

3. The process according to claim 2, wherein X is a sulfonyloxy selected from the group consisting of mesylate (Ms), tosylate (Ts) and triflate (Tf); or wherein X is an acetal represented by the structure CH(OR$^5$)$_2$ wherein each R$^5$ is independently a C1-C4 alkyl, or wherein CH(OR$^5$)$_2$ represents cyclic acetal, preferably 1,3-dioxane or 1,3-dioxolane.

4. The process according to claim 1, wherein in step (a) the formylating agent is selected from the group consisting of an alkyl formate, a trialkyl orthoformate and a formamidedialkylacetal derivative.

5. The process according to claim 1, wherein R$^1$ is methyl or ethyl and R$^2$ is methyl.

6. The process according to claim 1, wherein Y is OR$^2$ and the process comprises the steps of:

a). reacting a compound of formula (2) with a formylating agent selected from the group consisting of an alkyl formate and a trialkyl orthoformate to form a compound of formula (6):

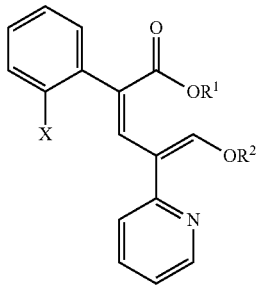
(6)

b). reacting compound (6) with aniline to form a compound of formula (7):

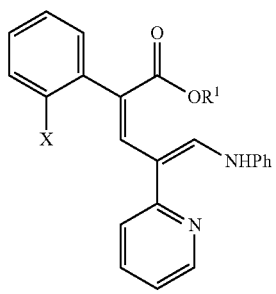
(7)

c). cyclizing the compound of formula (7) to a compound of formula (5)

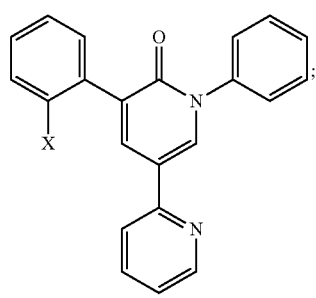
(5)

and d). converting of compound (5) to Perampanel (1).

7. The process according to claim 6, wherein the formylating agent in step (a) is a trialkyl orthoformate, and compound (2) is converted directly to compound (6).

8. The process according to claim 6, wherein the formylating agent in step (a) is an alkyl formate, and step (a) comprises the steps of:

(i) reacting a compound of formula (2) with an alkyl formate in the presence of a lewis acid so as to form an intermediate compound having an alcohol functionality;

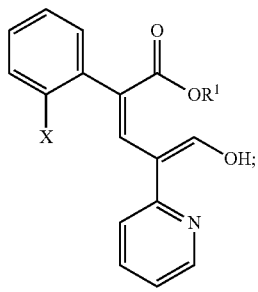

and (ii) alkylating the product obtained in step (i) with an alkylating agent in the presence of a base so as to form a compound of formula (6).

9. The process according to claim 1, wherein Y is $NR^3R^4$ and the process comprises the steps of:

a). reacting a compound of formula (2) with a formamidedialkylacetal derivative to form a compound of formula (8):

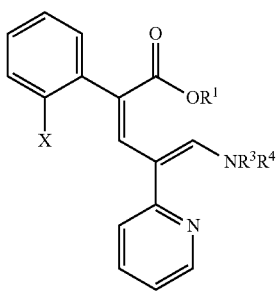

b). reacting compound of formula (8) with aniline to form a compound of formula (7):

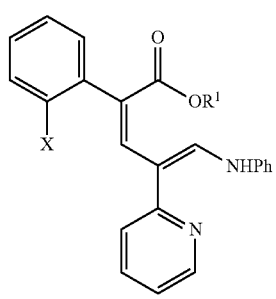

c). cyclizing the compound of formula (7) to form compound of formula (5):

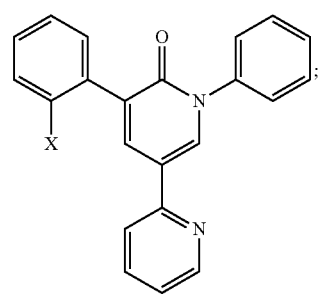

and d). converting compound (5) to Perampanel (1).

10. The process according to claim 1, wherein Y is $NR^3R^4$ and the process comprises the steps of:

a). reacting a compound of formula (2) with a formamidedialkylacetal derivative to form a compound of formula (8):

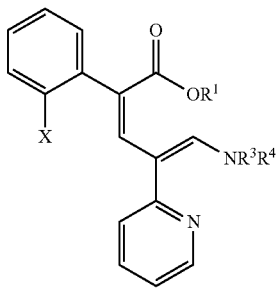

b1). reacting compound of formula (8) with an alcohol of formula $R^2$—OH to form a compound of formula (6):

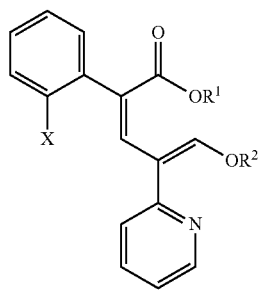

b2). reacting compound of formula (6) with aniline to form a compound of formula (7):

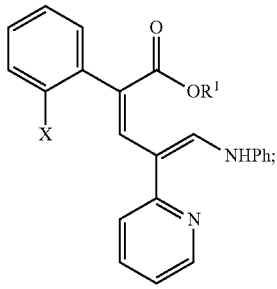

c). cyclizing the compound of formula (7) to form compound of formula (5):

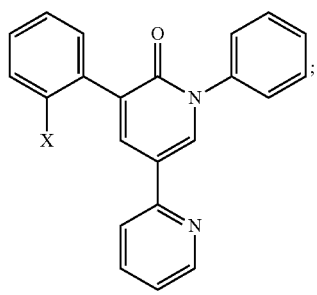

and d). converting compound (5) to Perampanel (1).

11. The process according to claim 10, wherein the formamidedialkylacetal derivative is dimethylformamide dimethyl acetal (DMF-DMA), or
    wherein $R^1$, $R^2$, $R^3$ and $R^4$ are each methyl or ethyl.

12. The process according to claim 1, wherein steps (b) and (c) are carried out as a single step by mixing compound (3) with aniline under heat resulting in a compound of formula (5).

13. The process according to claim 1, wherein X in compound (5) is an acetal represented by the structure $CH(OR^5)_2$ wherein each $R^5$ is a C1-C4 alkyl, or wherein $CH(OR^5)_2$ represents a cyclic acetal, preferably 1,3-dioxane or 1,3-dioxolane; and wherein step (d) comprises the following steps:
   (i). converting the acetal group of compound (5) to the corresponding aldehyde (X is CHO);
   (ii). reacting the aldehyde obtained in step (i) with hydroxylamine to form an oxime (X is CH=N—OH); and
   (iii) dehydrating the oxime formed in step (ii) to compound (1) (X is CN) in the presence of dehydration agent.

14. The process according to claim 13, wherein in step (i) deprotection of the acetal group of compound (5) to the corresponding aldehyde (X is CHO) is performed by acid catalyzed transacetalization in acetone or hydrolysis in wet solvents or in aqueous acid, or under neutral conditions in the presence of a catalytic amount of iodine.

15. The process according to claim 13, wherein in step (iii) the dehydration agent is selected from the group consisting of phosphorous oxychloride, thionyl chloride, triphosgene, propylphosphonic anhydride, ethyl dichlorophosphate, methanesulfonyl chloride, 2,4,6-trichloro-[1,3,5] triazine in N,N-dimethylformamide, chloral, Burgess reagent (methyl N-(triethylammonium-sulfonyl)carbamate), inorganic and organic acid anhydrides.

16. The process according to claim 1, further comprising the step of converting Perampanel to a pharmaceutically acceptable salt thereof.

17. The process according to claim 1, wherein the compound of formula (2) is prepared by reacting a phosphonium salt of formula (11) with a compound of formula (12) in the presence of a base:

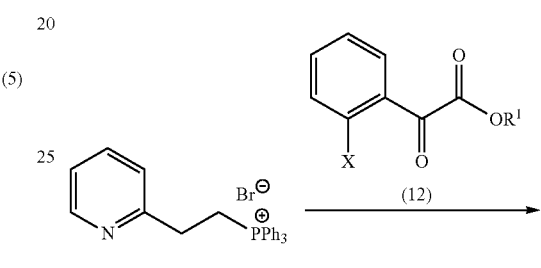

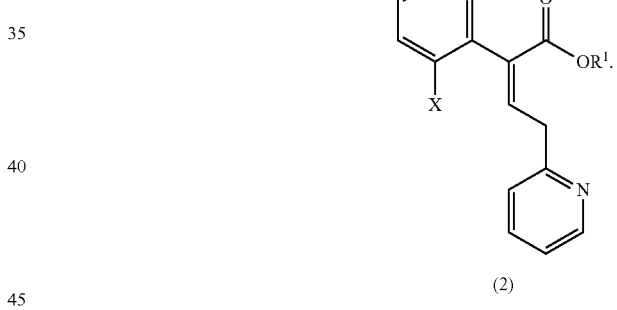

18. The process according to claim 17, wherein the base is selected from the group consisting of 1,8-diazabicyclo [5.4.0]undec-7-ene (DBU), 1,5-diazabicyclo[4.3.0]non-5-ene (DBN), 1,4-diazabicyclo[2.2.2]octane (DABCO), phosphazene, butyl-lithium, phenyl lithium, sodium amides, potassium amides, lithium diethylamide, lithium diisopropylamide, lithium piperidide, lithium, potassium bis(trimethylsilyl) amides and sodium bis(trimethylsilyl) amides and metal alkoxides.

19. The process according to claim 17, wherein the base is a metal alkoxide prepared directly in the reaction mixture (in-situ) by reacting a metal hydride with an alcohol.

20. A method of treating or preventing epilepsy or seizures, comprising the step of administering to a subject in need thereof an effective amount of the Perampanel or a salt thereof, which is produced in accordance with the process of claim 1, or a pharmaceutical composition comprising such compound.

21. A compound represented by the structure of formula (5);
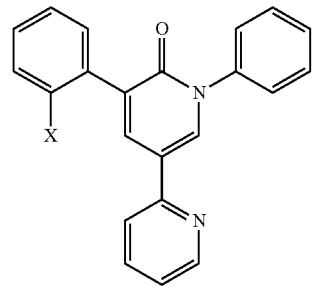
(5)
wherein X is a sulfonyloxy selected from the group consisting of mesylate (Ms), tosylate (Ts) and triflate (Tf); or
X is an acetal represented by the structure $CH(OR^5)_2$ wherein each $R^5$ is independently a C1-C4 alkyl, or wherein $CH(OR^5)_2$ represents cyclic acetal, preferably 1,3-dioxane or 1,3-dioxolane.
* * * * *